United States Patent [19]

Meibauer

[11] Patent Number: 4,727,894

[45] Date of Patent: Mar. 1, 1988

[54] DENTAL PROPHYLAXIS DEVICE AND PROCESS

[76] Inventor: Robert H. Meibauer, 234 Rte. 537 East, Colts Neck, N.J. 07722

[21] Appl. No.: 706,649

[22] Filed: Feb. 28, 1985

[51] Int. Cl.[4] ............................................. A61C 15/00
[52] U.S. Cl. ...................................... 132/91; 433/122
[58] Field of Search .................. 132/89, 90, 91, 92 R, 132/92 A, 93; 15/167 R, 167 A; 433/122, 123

[56] References Cited

U.S. PATENT DOCUMENTS

| | | | |
|---|---|---|---|
| 557,523 | 3/1896 | Brown | 433/122 |
| 2,601,567 | 6/1952 | Steinberg | 15/22 |
| 3,421,524 | 1/1969 | Waters | 132/92 |
| 3,534,745 | 10/1970 | Waters | 132/92 |
| 3,552,022 | 1/1971 | Alexsson | 433/122 |
| 3,667,454 | 6/1972 | Prince | 15/167 R |
| 3,667,483 | 6/1972 | McCabe | 132/92 A |
| 3,759,274 | 9/1973 | Warner | 132/92 R |
| 3,828,804 | 8/1974 | Ely | 132/91 |
| 3,835,872 | 9/1974 | Daniel | 132/92 R |
| 3,901,251 | 8/1975 | Johnston | 132/91 |
| 3,927,686 | 12/1975 | Zambito | 132/92 R |
| 4,014,354 | 3/1977 | Garrett | 132/90 |
| 4,162,687 | 7/1979 | Lorch | 132/91 |
| 4,307,740 | 12/1981 | Florindez et al. | 132/92 R |
| 4,338,957 | 7/1982 | Meibauer | 132/91 |

Primary Examiner—John J. Wilson
Attorney, Agent, or Firm—Morgan & Finnegan

[57] ABSTRACT

There is disclosed a dental prophylaxis device having a pair of spaced tynes disposed on a housing provided with an axial cavity, a stationary support located on the tynes in the vicinity of the base thereof and a circular rotatable disk located on the housing between the bases of the tynes. The circular rotatable disk rotates on a mandrel disposed in the housing cavity through a rotatable drive shaft located in a second housing. A dental flossing thread having a non-elastic loop at one end supported on the circular rotatable disk and an elastic loop on the opposite end supported on the stationary support spans the space between the ends of tynes and reciprocates therebetween when the disk is rotated.

The process comprises contacting dentition surfaces with the dental flossing thread described and reciprocating the thread over the dentition surfaces and across the space between the stationary tynes while expanding and contracting the elastic loop in response to the tensile force on the thread and absorbing the tensile force imparted thereto when it encounters resistance and while imparting reciprocating movement to the dental flossing thread through the rotating motion of the disk.

10 Claims, 6 Drawing Figures

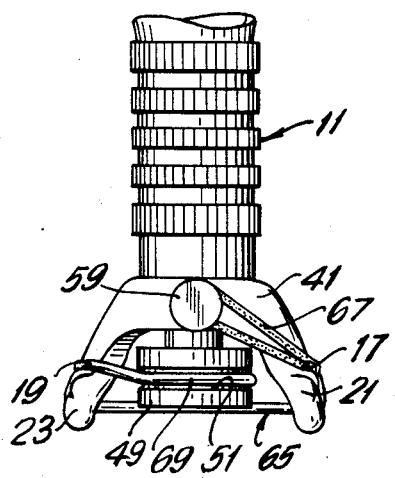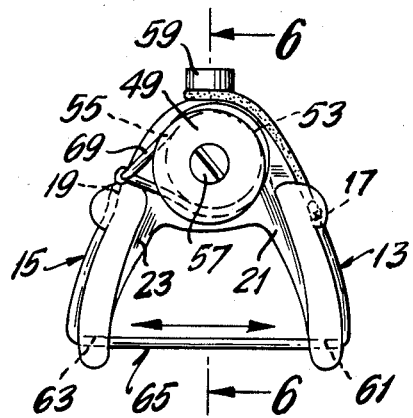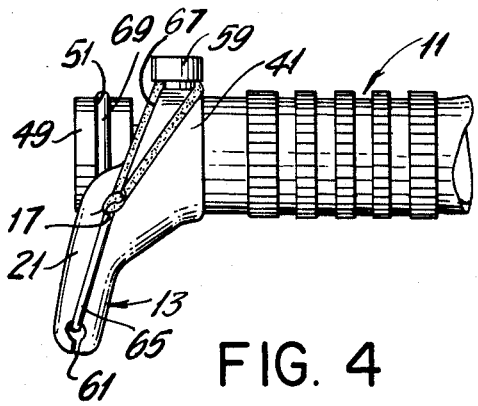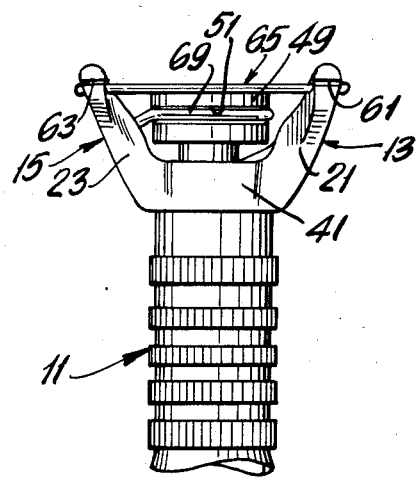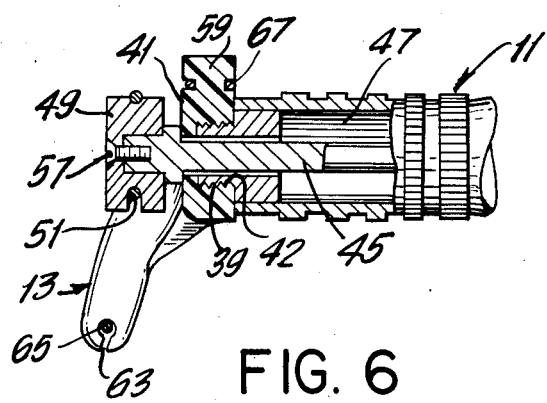

DENTAL PROPHYLAXIS DEVICE AND PROCESS

This invention relates to a dental prophylaxis device and a dental prophylaxis process. More particularly, the invention relates to a mechanical device for the flossing of dentition surfaces and a dental flossing process.

BACKGROUND OF THE INVENTION

It is well known in the field of dentistry that failure to remove plaque from dentition surfaces and debris from between dentitions is a principal cause of dental diseases, such as tooth decay and gingivitis and the like. Removal of plaque and debris by brushing is the commonest and easiest method known. However, brushing is generally inadequate, especially when self-administered. A more efficient and known technique is the cleaning of the dentition surfaces and areas between such surfaces by using a dental tape or floss which is moved reciprocally over and between the dentition surfaces. Furthermore, the reciprocating motion of the floss as its manipulated over and between the dentition surfaces is beneficial as a treatment for and prevention of periodontal diseases, such as gingivitis and the like. This is so since the free margin of the gingiva which is adjacent to the individual teeth of the dentition and forms the gingival sulcus can be readily reached by dental floss, although it is generally inaccessible to a brush or other instruments, and the sulci are subject to the invasion of plaque or colonies of bacteria which cause diseases of these tissues. Thus, floss, in general, is particularly beneficial in removing plaque and debris, as well as serving, in addition, as a vehicle for the the application of medication. On the other hand, dental tape or floss is inconvenient and akward to handle.

Consequently, much development has been undertaken in the past to provide dental tape or floss in various forms which is more convenient to handle and use. In addition, much development has taken place to provide mechanical devices for the flossing of dentition surfaces. Therefore, past developments have broadly involved the provision of dental tape or floss in various forms to render the same easier to use and the provision of mechanical devices to support or hold the dental tape or floss in a manner so that it can be employed with greater efficiency and facility.

As an example of such developments, U.S. Pat. No. 4,162,687 discloses a flossing device which is manipulated by hand and provided with a pair of spaced, resilient arms having fingers extending therefrom. The fingers are equipped with knobs on their distal ends and a length of dental tape or floss having a grommet on each end is disposed over the knobs on the ends of the fingers. A somewhat similar device, but which is power driven, is disclosed in U.S. Pat. No. 4,014,354 in which the dental tape or floss is tensioned between a pair of L-shaped arms attached to a handle which is adapted to be driven by the power element. On the other hand, U.S. Pat. No. 3,927,686 discloses a hand manipulated flossing device which includes a handle and an adjustable head provided with a single strand or a plurality of strands of dental tape or floss.

Still another dentition cleaning device is disclosed in U.S. Pat. No. 3,835,872 in which a flexible dental tape or floss is disposed on a handle having a detachable yoke for tautly supporting a run of the tape, the tape being attached to a pair of anchor pins disposed on the handle and one of which is disposed on a reciprocable trigger mounted in the handle for the purpose of tensioning the tape. The tape per se is provided with nonelastic loops at each end which are disposed over the previously mentioned pins. U.S. Pat. No. 3,828,804 discloses still another apparatus which is a hand manipulated device for cleaning teeth that includes a handle with a nub disposed thereon and which is provided with extending, spaced arms having notches at the ends thereof. An endless or circular elastomeric dental floss or tape is disposed in the notches thereby passing across the space between the arms and around the nub. In a variation of the device a simple length of elastomeric band is anchored in the notches of the arms by means of shims or heads.

A further dentition cleaning instrument is disclosed in U.S. Pat. No. 3,759,274 in which a strand of dental floss is mounted on an extended fork which supports the strand and permits an oscillating movement which is imparted thereto by a drive means. In addition, the device also includes a spool for carrying the strand and for registering a new, unused portion of the strand for use in each subsequent cleaning cycle. A still further dentition cleaning device is shown in U.S. Pat. No. 3,667,483 in which the device includes a pair of projecting arms disposed on a support frame, the arms being provided with guides at their outer ends to receive and permit relative movement of floss which passes from a spool to a take-up reel mounted on the supporting frame. The floss is driven in a reciprocating manner through a device provided with means to alternately remove floss from the supply spool and feed it to the take-up spool after each use.

In U.S. Pat. No. 3,552,022 there is disclosed another powered dentition cleaning or polishing device in which a tool having a conical stem portion is adapted to be inserted in and removed from a handle in which a reciprocating socket is provided therefor. The operating end of the tool is wedgelike and pointed, two broad sides being rough in order to abrade dentition surfaces and a third side thereof being narrow and smooth in order to prevent injury to the gingiva. Another power driven cleaning device is disclosed in U.S. Pat. No. 3,534,745. The device includes a housing provided with spaced prongs and a dental tape or floss holder and supply unit adapted to be removably attached to a power unit which imparts reciprocating motion to the tape as well as permitting the feeding of new tape to the unit after each use. Finally, U.S. Pat. No. 3,421,524 discloses a power driven dentition cleaning device including a power unit which is adapted to receive a cleaning unit which includes an elongated shaft provided with a pair of spaced tynes. A dental tape or floss supply holding member is removably positioned on the power unit and the dental tape or floss is fed therefrom through an eyelet in each of the tynes and back to the supply holding member where it is taken up on a take-up spool.

While the various devices disclosed in the above-mentioned patents are useful for cleaning dentition surfaces, they still exhibit various disadvantages. For example, many of them are extremely complex in structure and consequently relatively expensive to manufacture. In addition, many of the known structures are relatively difficult to employ, often being difficult to load and requiring complex adjustment to impart the required tenseness to the dental tape or floss utilized therewith.

In addition, many of the known devices, such as those referred to above, are not provided with means to automatically stop the movement of the floss should it become caught or jammed on the dentition surfaces. Furthermore, due to their particular construction, many of the known devices do not provide maximum contact of the floss with the dentition surfaces to be cleaned and, in addition, due to their construction, necessitate the use of more than the needed amount of dental tape or floss for carrying out a given cleaning operation.

The disadvantages of the above-described devices have been substantially completely eliminated by the device and process of my U.S. Pat. No. 4,338,957 of July 13, 1982. In that patent there is disclosed a dental prophylaxis device which comprises in combination housing means provided with an axial cavity and having a pair of spaced tynes provided with slotted openings disposed thereon and projecting outwardly therefrom, stationary support means on the housing in the vicinity of the base of each of the tynes and oscillating support means located on the housing between the bases of the tynes and which is supported on a cylindrical sleeve that is disposed axially within the cavity of the housing, the housing means being adapted to be connected to driving means to drive the oscillating support means through the cylindrical sleeve.

The dental prophylaxis process comprises contacting dentition surfaces to be treated with a dental floss having a thread segment which is provided with a non-elastic loop at one end and an elastic loop at the opposite end, reciprocating the thread segment over the surfaces of the dentition to be treated, while expanding and contracting the elastic loop in response to the application of tensile force to the dental floss as it reciprocates over the dentition surfaces and absorbing the tensile force which is imparted to the dental floss when it encounters resistance as it reciprocates over the dentition surfaces and the elastic loop expands.

While my previous device and process have substantially completely eliminated the disadvantages of the above-described devices, there still exists, however, the need for such a device and process which exhibit even further improvement. The present invention fulfills this need.

BRIEF STATEMENT OF THE INVENTION

In accordance with the invention there is provided a device for dental prophylaxis which in its broadest terms comprises in combination housing means provided with an axial cavity, a pair of spaced stationary tynes provided with slotted openings disposed on the housing means and projecting outwardly therefrom, stationary support means located on the tynes in the vicinity of the base thereof, rotatable eccentric support means located on the housing means between the bases of the tynes supported on a rotatable mandrel disposed axially within the cavity of the housing means and the rotatable mandrel being adapted to be connected to driving means to drive the rotatable eccentric support means.

In a more detailed aspect, a device for dental prophylaxis according to the invention includes second housing means removably connected to the first housing means having rotatable driving means located therein.

In a still further detailed aspect, a dental prophylaxis device in accordance with the invention comprises housing means provided with an axial cavity, stationary tynes provided with slotted openings disposed on the housing means and projecting outwardly therefrom, stationary support means located on the tynes in the vicinity of the base thereof and a circular rotatable disk located on the housing means between the bases of the tynes and centrally supported on a rotatable mandrel disposed axially within the cavity of the housing. The disk has a groove disposed around the circumference thereof which is shallow in one portion and deep in the portion opposite the shallow portion and the rotatable mandrel is adapted to be connected to driving means to drive the circular rotatable disk and impart rotating motion thereto; and dental flossing thread provided with a non-elastic loop at one end and an elastic loop at the opposite end supported in the slotted openings of the tynes and across the space therebetween with the elastic loop being supported on the stationary support means and the non-elastic loop being supported in the circumferential groove of the disk, whereby the dental flossing thread reciprocates between the tynes when the disk is rotated by the driving means through the rotatable mandrel.

Further, in accordance with the invention, the dental prophylaxis process comprises contacting dentition surfaces to be treated with a dental floss having a thread segment provided with a non-elastic loop at one end and an elastic loop at the opposite end, reciprocating the thread segment over the dentition surfaces and across the space between a pair of spaced, stationary tynes bracketing the dentition surfaces while imparting movement to the non-elastic loop along an axial line which is substantially at a right angle to the axis of reciprocation of the thread segment across the space between the tynes through rotary motion of a rotatable eccentric support means rotating on an axial line which is substantially at a right angle to the axes of reciprocation of the non-elastic loop and the thread segment and while expanding and contracting the elastic loop in response to the application of tensile force to the dental floss as it reciprocates over the dentition surfaces, and absorbing the tensile force imparted to the dental floss when it encounters resistance as it reciprocates over the dentition surfaces and the elastic loop expands.

THE DRAWINGS

In order to describe the device and process of this invention more fully, reference is directed to the accompanying drawings which are to be taken in conjunction with the following description and in which drawings:

FIG. 2 is a partial, plan view of the device shown in FIG. 1;

FIG. 3 is a front end view in elevation of the device in FIG. 1;

FIG. 4 is a partial, elevational view of the device shown in FIG. 1;

FIG. 5 is a partial, bottom view of the device shown in FIG. 1; and

FIG. 6 is a partial, elevational view of the device shown in FIG. 1, partially in section, illustrating in detail the rotatable mandrel disposed within the housing cavity, the attachment of the tynes to the housing and the attachment of the rotatable eccentric support means to the rotatable mandrel and which is taken across Line 6—6 of FIG. 3.

DESCRIPTION OF THE PREFERRED EMBODIMENTS

Figure 1:
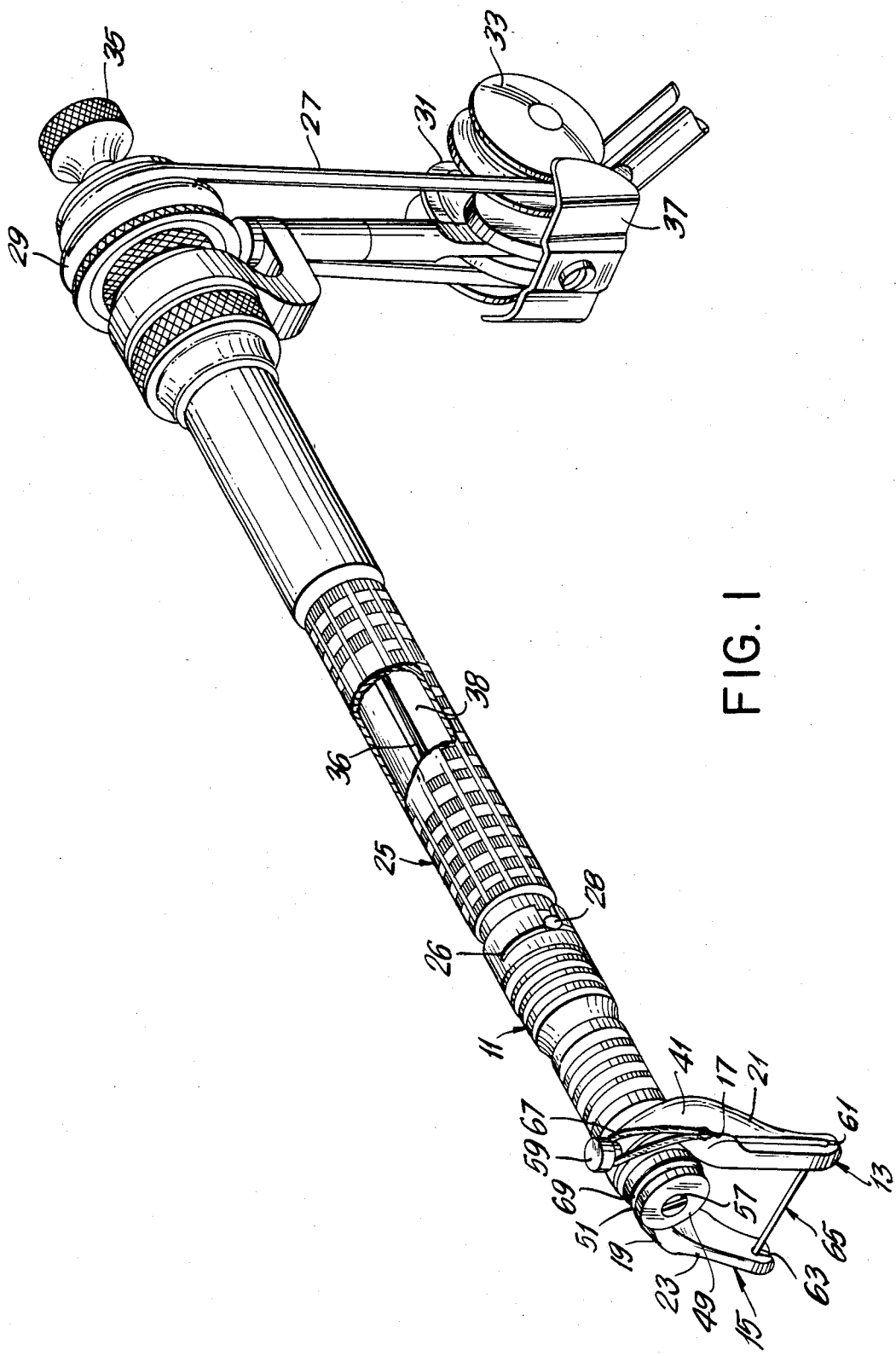
FIG. 1 is a view in perspective and partially in section of a dental prophylaxis device according to the invention showing in part the arrangement for driving the driving means.

Referring now to FIG. 1, a dental prophylaxis device according to the invention comprises an elongated generally tubular housing 11 having a pair of tynes 13 and 15 disposed thereon at one end. The tynes are provided with guide grooves 17 and 19, respectively, on their shoulders 21 and 23. At the opposite end, housing 11 is adapted to be connected and locked to a second elongated tubular housing 25, such as a standard dental handpiece, by means of a slot 26 in housing 11 which cooperates with a pin 28 on housing 25. Housing 25 is also equipped with an appropriate driving belt 27, guide pulleys 29, 31 and 33, adjusting knob 35 and a keeper 37 for holding the driving belt 27 in proper disposition with respect to the pulleys. Knob 35 is attached to an elongated axially disposed driving means such as a driving rod 36 located in a central axial cavity 38 of housing 25, as is well known in the art. Driving belt 27 is adapted to be driven by an appropriate source of power, such an as electrically or battery driven motor or the like (not shown). It is to be understood that while a preferred embodiment of this invention includes the dental handpiece, as housing 25, it is within the purview of this invention that the dental handpiece can be replaced by an appropriately designed electric or battery powered unit handpiece or housing, such as, for example, that shown in U.S. Pat. No. 4,338,957 in order to energize the device.

As may be seen in greater detail in FIG. 6, housing 11 is provided with a threaded end portion 39 and the base 41 of the tynes is provided with a central threaded opening 42 in order to fix the tynes to the housing. A rotating mandrel 45 is axially disposed in the axial cavity 47 of housing 11 and is adapted to be connected to the driving rod of the dental handpiece or housing 25 in a conveniently appropriate manner, as mentioned above. A circular rotatable support means or disk 49 is centrally fixed to the outer end of the mandrel 45 between the bases of the tynes. Disk 49 is provided with a circumferential groove 51 which is shallow in one portion 53 and deeper in the portion 55 opposite the shallow portion, as shown in FIG. 3. Disk 49 may be fixed to mandrel 45 in any convenient manner, such as by screw 57 or the like, thus turning when the mandrel is rotated.

Stationary support means, such as post 59, is located on the base of the tynes which are provided with slotted openings 61 and 63. A dental tape or floss 65 provided with an elastic loop 67 at one end, which is supported on post 59, and a non-elastic loop 69 at the opposite end, which is supported in the groove 51 of disk 49, extends across the space between the tynes and is supported in slots 61 and 63 and guide grooves 17 and 19 of the tynes.

The various elements of the dental prophylaxis device of this invention, excluding the tape or floss may be made from a wide variety of materials, either metals or plastics. Generally, the housing elements and parts associated therewith are preferably made of metals, such as steel and the like. In contrast, the tynes and associated parts, as well as the circular rotable support or disk are preferably made of plastics materials. In general, plastics such as nylon, polyester and the like are preferred since they can be more readily shaped or molded at a lower cost while still exhibiting the required strength.

Insofar as the tape or floss is concerned, it can be made from natural of synthetic thread material, such as, for example, cotton and nylon, and the like with a non-elastic loop attached in any convenient manner to one end and an elastic loop, such as, tor example, a rubber band, attached in any convenient manner at the opposite end. Alternatively, and preferably, the tape or floss can be made from a synthetic thread having alternate non-elastic and elastomeric segments cut into the desired premeasured lengths to provide individual lengths of floss having a non-elastic segment and an elastomeric segment at opposite ends and then forming the non-elastic loop and elastomeric loops at each end by employing the respective non-elastic and elastomeric ends turned back upon themselves and joined in any convenient manner.

Now, while it is contemplated that the dental prophylaxis device of the invention will be utilized with a dental handpiece such as housing 25 and the associated parts thereof, thus being employed in a dental office by professionally trained personnel, it is also within the purview of this invention to market the device for use by the ultimate consuming public. In such cases, the dental handpiece would be replaced by an appropriately designed electric or battery operated housing which contains the driving means. In this respect, an ultimate consumer will normally obtain or purchase the whole device, that is, the housing 11, the appropriately designed second housing 25 and at least one dental tape or floss. On the other hand, an ample supply of tapes can also be provided with the initial purchase or sold separately at a later time. Moreover, a member of the consuming public who has already undertaken the initial purchase can, if needed, simply purchase at a subsequent time, either the housing 11 and the parts associated therewith, or the housing 25, should replacement parts be needed or desired for one reason or another. In this regard, where a device is to be employed by a number of individuals in a household, only one housing 25 may be purchased along with an adequate supply of tapes and a sufficient number of housing 11 to accomodate each individual member of the household, or, if desired, one may only puchase one housing 11 and a sufficient number of circular rotatable disks, including mandrels and a sufficient number of tynes so that each individual member of a household may have for his individual use the portions of the device which are generally inserted into the mouth during use. As is evident from the above description of the device, the tynes and circular rotatable disk, including the mandrels, can be readily assembled and disassembled with the housing 11. The obvious hygienic advantages achieved by purchase of a separate set of tynes and a circular rotatable disk and mandrel for each individual user are evident.

Turning once again to the circular rotatable support means or disk 49, as described hereinbefore, it is to be noted that the circumferential groove 51 therein, in its shallow portion 53 should be at least deep enough so that the non-elastic loop 69 of the tape or floss 65 does not become dislodged therefrom as the disk rotates. In general, the groove will be sufficiently deep at its shallow portion so that it accomodates substantially completely the diameter of the non-elastic loop portion of the thread. On the other hand, the depth of the groove opposite the shallow portion thereof where it is at its deepest has an effect upon the distance of reciprocation of the floss or thread between the ends of the tynes. The depth of the slot and the distance of reciprocation of the floss are directly proportional to each other. In practice, it has been found that a disk having a 7 mm diameter and provided with a 2 mm central opening to accomodate the screw and the shaft of the mandrel to which the disk is fixed and which has a circumferential groove 2 mm deep at its greatest depth will provide 2 mm distance of reciprocation of the floss or thread between the ends of the tynes. The 2 mm distance of reciprocation has been found in use to provide a sufficient amount of movement of the floss so that excellent flossing results are obtained.

The unique construction of the disk, that is with respect to the groove being shallow in one portion and deeper in the portion opposite the shallow portion, provides a unique result in the operation of the device since a disk so made operates in an eccentric fashion while rotating on the mandrel while at the same time imparting a reciprocating motion of the dental thread or floss across the space between the tynes. Consequently, as the disk rotates through its high point, the elastic loop 67 of the dental floss or thread fixed to the post 59 stretches, thus permitting the portion of the floss or thread between the tynes to move first in one direction and as the disk rotates through the point of greatest depth of the groove, the elastic loop will contract, thus pulling the tape in the opposite direction.

In accordance with the inventive concept of this invention, the depth of the groove can be varied in order to adjust the distance of reciprocation of the floss or thread between the tynes. It is generally preferred, however, that the deepest portion of the groove by about 2 mm since this gives a sufficient reciprocating distance of movement to the floss or thread to impart required flossing results to dentition surfaces on which the device is being employed. Should the depth be increased or decreased, the reciprocating distance will be either increased or decreased and also either less beneficial or more beneficial flossing results may be obtained. In such cases, flossing results are still more advantageous than not flossing at at. However, as previously mentioned, a groove having a depth of about 2 mm at the greatest, has been found to provide excellent flossing results.

In use, the dental prophylaxis device in this invention operates in the following manner. When the housing 11 is connected to a dental handpiece, such as housing 25, and the device is energized, either through a battery or electrical means, as mentioned above, imparting power to the driving means through the driving belt 27, the mandrel 45 rotates, thus rotating the circular rotatable disk 49 which, as it rotates through the high point of groove 51, extends the elastic loop 67 of the dental floss or thread, thus moving the floss or thread in one direction between the ends of the tynes. As the disk continues its rotation and passes through the point of greatest depth of the groove, the elastic loop will retract, pulling the floss or thread in the opposite direction between the tynes. This cycle of operation continues as the disk rotates imparting a reciprocating motion to the thread in the space between the tynes, the speed of reciprocation being dependent upon the speed of rotation which can be adjusted at will by accelerating or decelerating the power means being utilized to energize the device.

In use, the speed of reciprocation of the dental prophylaxis device of this invention can be varied greatly. In general, however, it is preferred that the dental floss or thread be reciprocated between the ends of the tynes at a speed at about 5 mm per second to about 8 mm per second for best flossing results. While lesser or greater speeds of reciprocation per second can be utilized, the best flossing results are obtained when the device is operated within the above mentioned range.

In utilizing the device and carrying out the process of this invention, medication may, if desired, be applied to the dental floss and transferred to the dentition surfaces over which the floss reciprocates. Consequently, in this respect, the process of this invention in its more specific aspects also includes the application of such medication to the dentition surfaces being treated.

The dental prophylaxis device and process of this invention present numerous advantages. For example, the device, due to its unique construction, utilizes rotary motion of the disk to impart reciprocating motion to the floss or thread. Moreover, the reciprocating motion imparted to the thread or floss is imparted thereto in a smooth even manner so that the flossing activity of the floss or thread takes place without causing any discomfort to a user. Furthermore, the unique construction of the floss or thread per se also aids in imparting a smooth reciprocating motion to the floss or thread since the elastic loop acts to provide a source of constantly varying tension to the floss or thread as it reciprocates between the tynes. At the same time, the non-elastic loop thereof moves smoothly and evenly in a direction substantially vertical to the direction of reciprocation of the floss or thread due to the eccentric path followed by the groove as the disk moves in a rotary direction.

Still further, the unique combination of elements of a dental prophylaxis device, in accordance with this invention, and especially the utilization of the floss or thread having an elastic loop on one end, provides "built in" tension control of the floss, as well as positive return to a start position. The positive "built in" tension control of the floss assures maximum contact thereof with dentition surfaces being treated at all times. Consequently, point to point contact of dentition surfaces and floss, which occurs if the thread is too tense,or no action at all if the thread is too slack, is substantially eliminated. At the same time, however, the proper positive tension resulting from the use of the elastic loop on the floss or thread permits the floss to stop reciprocating even though the power is on in the event the thread becomes caught or jammed on the dentition surfaces being treated.

Still further, the provision of proper positive tension on the floss or thread by use of the elastic loop substantially eliminates irritation, which often occurs with known flossing devices due to excessive tension imparted to the floss by such devices. Finally, the use of tape or floss segments with looped ends and the ease with which it can be attached or fixed to the prophylaxis device of this invention eliminates extensive handling of the dental floss or thread and is thus more hygienic.

Insofar as the housings and related elements of the device are concerned, they are relatively easy and inexpensive to manufacture with readily available materials and a plurality of the housing portions provided with the tynes can be sold for use with one driving means. Moreover, the housing portion having the tynes can also be sold, separately and adapted for attachment for use with equipment normally found in a dental office. Furthermore, since the tynes are stationary and only the tape or floss reciprocates, the device is easier to employ without the danger of damaging dentition surfaces by contact thereof with the tynes, as is the case with devices which have to be manipulated by hand in the mouth of a user in order to reciprocate or otherwise move the tape or floss.

It is to be understood that the device and process of this invention provide a mechanical flossing means for the removal of plaque on the inter-proximal surfaces of the teeth and, as such, are much more efficient than hand flossing methods. Moreover, the device and process of this invention eliminate many of the problems inherent in previous devices since the tapes or floss can be attached to the mechanical portions of the device in a matter of seconds and the unique structure of the floss loops eliminates previous means of securing floss by winding and the like. With the device and in accordance with the process, the floss moves rapidly and conforms to the contours of the dentition surfaces without loss of speed or creating slack as often occurs in known devices and the entire dentition surface can be flossed efficien1tly in a matter of minutes. Furthermore, as previously mentioned, the tynes do not move as in some known devices, thus obviating the danger of damaging tissue and dental surfaces by abnormally sharp contact of the tynes therewith.

It is also to be noted that the device can be used advantageously by all age groups, from preschool age children to adults and moreover, the device can be utilized with great facility by a parent to floss a child's teeth. In addition, the entire device is easily cleaned or sterilized, thus providing hygienic benefits. The loops, due to their low cost, are disposable after use, thus also providing increased hygiene standards.

The reciprocal action of the tape or floss is beneficial in treating and preventing periodontal disease, that is, gingivitis, since the sulci between the teeth can be reached easily by the dental tape used with the device. Moreover, the mechanical action of the device, in accordance with the process, debrides the tissues of bacterial colonies, necrotic tissue and organic debris, accomplishing this without irritation, while at the same time providing a stimulating effect which promotes the formation of the hornified layer of cells that normally protects the underlying tissues from trauma and bacterial invasion. Numerous other advantages of the inventive device and process will be readily apparent to those skilled in the art.

It is to be understood that the descriptive embodiments of this invention set forth herein are illustrative only and the concepts of this invention are not to be limited thereby, except as defined in the appended claims.

What is claimed is:

1. In a device for dental prophylaxis, the combination comprising:
   housing means provided with an axial cavity, a pair of spaced, stationary tynes provided with slotted openings disposed on said housing means and projecting outwardly therefrom, stationary support means located on said tynes in the vicinity of the base thereof and a circular rotatable disk located on said housing means between the bases of said tynes and centrally supported on a rotatable mandrel disposed axially within said cavity, said disk having a groove disposed around the circumference thereof which is shallow in one portion and deep in the portion opposite the shallow portion, said rotatable mandrel being adapted to be connected to driving means to drive said circular, rotatable disk and impart rotating motion thereto; and dental flossing thread provided with a non-elastic loop at one end and an elastic loop at the opposite end supported in said slotted openings of said tynes and across the space therebetween with said elastic loop being supported on said stationary support means and said non-elastic loop being supported in the circumferential groove of said disk, whereby said dental flossing thread reciprocates between said tynes when said circular, rotatable disk is rotated by said driving means through said rotatable mandrel.

2. A device according to claim 1 wherein each of the pair of spaced tynes is provided with a guide groove on the external shoulder thereof.

3. A device according to claim 1 wherein the housing means is adapted to be removably connected to second housing means having rotatable driving means located therein.

4. A device according to claim 3 wherein the second driving means is a dental handpiece.

5. A device according to claim 1 wherein the driving means is electrically powered.

6. A device according to claim 1 wherein the driving means is battery powered.

7. In a device for dental prophylaxis, the combination comprising:
   first and second housing means removably connected to each other, said first housing means provided with an axial cavity, a pair of spaced, stationary tynes provided with slotted openings and a guide groove on the external shoulder of each tyne of said pair disposed on said housing and projecting outwardly therefrom, stationary support means located on said tynes in the vicinity of the base thereof and a circular rotatable disk located on said first housing means between the bases of said tynes and centrally supported on a rotatable mandrel disposed axially within said cavity, said disk having a groove disposed around the circumference thereof which is shallow in one portion and deep in the portion opposite the shallow portion, said rotatable mandrel being adapted to be connected to driving means to drive said circular, rotatable disk and impart rotating motion thereto; said second housing means provided with an axial cavity having said driving means axially disposed therein adapted to be connected to said first housing means; and dental flossing thread provided with a non-elastic loop at the opposite end supported in said slotted openings of said tynes and across the space therebetween with said elastic loop being supported on said stationary support means and said non-elastic loop being supported in the circumferential groove of said disk, whereby reciprocating movement is imparted to said dental flossing thread across the space between said tynes and reciprocating movement is imparted to said non-elastic loop along an axial line which is substantially at a right angle to the axis of reciprocation of said dental flossing thread through rotating motion of said disk on an axial line substantially at a right angle to the axes of reciprocation of both said non-elastic loop and said dental flossing thread when said device is in an operating condition.

8. A device according to claim 7 wherein the second driving means means is a dental handpiece.

9. A device according to claim 7 wherein the driving means is electrically powered.

10. A device according to claim 7 wherein the driving means is battery powered.